(12) United States Patent
Sealey et al.

(10) Patent No.: US 10,190,260 B2
(45) Date of Patent: Jan. 29, 2019

(54) FLUFF PULP AND HIGH SAP LOADED CORE

(71) Applicant: INTERNATIONAL PAPER COMPANY, Memphis, TN (US)

(72) Inventors: James E. Sealey, Anderson, SC (US); Brent A. Fields, Trenton, OH (US)

(73) Assignee: INTERNATIONAL PAPER COMPANY, Memphis, TN (US)

( * ) Notice: Subject to any disclaimer, the term of this patent is extended or adjusted under 35 U.S.C. 154(b) by 0 days.

(21) Appl. No.: 15/852,746

(22) Filed: Dec. 22, 2017

(65) Prior Publication Data

US 2018/0142414 A1   May 24, 2018

Related U.S. Application Data

(62) Division of application No. 13/964,322, filed on Aug. 12, 2013, now Pat. No. 9,869,059.

(Continued)

(51) Int. Cl.
*D21H 11/00* (2006.01)
*D21H 17/36* (2006.01)
(Continued)

(52) U.S. Cl.
CPC ............. *D21H 11/00* (2013.01); *D04H 1/732* (2013.01); *D06C 15/00* (2013.01); *D21H 17/36* (2013.01);
(Continued)

(58) Field of Classification Search
CPC ...... D21H 21/22; D21H 11/00; D21H 17/375; D21H 17/36; D21H 17/37; D21H 17/06; D04H 1/732; D04H 1/26; A61F 2013/530014; A61F 2013/530021; A61F 2013/530481; A61F 2013/530489; A61F 13/5323; A61F 47/38; D06C 15/00; Y10S 428/92; Y10T 428/27

See application file for complete search history.

(56) References Cited

U.S. PATENT DOCUMENTS 3,994,771 A   11/1976   Morgan et al.
4,022,965 A   5/1977   Goheen et al.
(Continued)

FOREIGN PATENT DOCUMENTS

CA   2881426 A1 *   2/2014   ............ D04H 1/732
CN   1053544            8/1991
(Continued)

OTHER PUBLICATIONS

Office Action dated Sep. 16, 2016 as received in U.S. Appl. No. 13/964,322.
(Continued)

*Primary Examiner* — Jose A Fortuna
(74) *Attorney, Agent, or Firm* — Clifford R. Lamar, II; Thomas W. Barnes, III

(57) ABSTRACT

A fluff pulp is provided, which comprises softwood fibers; and 3 to 35% by weight of hardwood fibers. A fluff is also provided, which comprises the fiberized or shredded fluff pulp. A core is also provided, which comprises the fluff and at least an SAP. Processes for making and using the fluff pulp, fluff, and core are provided, and products made thereby.

9 Claims, 6 Drawing Sheets

Related U.S. Application Data

(60) Provisional application No. 61/681,799, filed on Aug. 10, 2012.

(51) Int. Cl.
*D21H 17/37* (2006.01)
*D21H 21/22* (2006.01)
*D04H 1/732* (2012.01)
*A61F 13/00* (2006.01)
*D06C 15/00* (2006.01)
*A61F 13/53* (2006.01)

(52) U.S. Cl.
CPC ........... *D21H 17/37* (2013.01); *D21H 17/375* (2013.01); *D21H 21/22* (2013.01); *A61F 2013/530014* (2013.01); *A61F 2013/530021* (2013.01); *A61F 2013/530481* (2013.01); *A61F 2013/530489* (2013.01)

(56) References Cited

U.S. PATENT DOCUMENTS

| | | | |
|---|---|---|---|
| 4,075,136 A | 2/1978 | Schaper | |
| 4,166,894 A | 9/1979 | Schaper | |
| 4,174,417 A | 11/1979 | Rydell | |
| 4,425,186 A | 1/1984 | May et al. | |
| 4,431,481 A | 2/1984 | Drach et al. | |
| 4,496,427 A | 1/1985 | Davison | |
| 4,929,480 A | 5/1990 | Midkiff et al. | |
| 4,986,882 A | 1/1991 | Mackey et al. | |
| 5,049,235 A | 9/1991 | Barcus et al. | |
| 5,160,789 A | 11/1992 | Barcus et al. | |
| 5,209,953 A | 5/1993 | Grupe et al. | |
| 5,266,250 A | 11/1993 | Kroyer | |
| 5,294,478 A | 3/1994 | Wanek et al. | |
| 5,360,420 A | 11/1994 | Cook et al. | |
| 5,443,899 A | 8/1995 | Barcus et al. | |
| 5,516,569 A | 5/1996 | Veith et al. | |
| 5,531,728 A | 7/1996 | Lash | |
| 5,562,645 A * | 10/1996 | Tanzer | A61F 13/15203 604/358 |
| 5,662,773 A | 9/1997 | Frederick et al. | |
| 5,667,637 A | 9/1997 | Jewell et al. | |
| 5,698,074 A | 12/1997 | Barcus et al. | |
| 5,698,688 A | 12/1997 | Smith et al. | |
| H1704 H | 1/1998 | Wallajapet et al. | |
| 5,731,080 A | 3/1998 | Cousin et al. | |
| 5,776,308 A | 7/1998 | Sears et al. | |
| 6,086,950 A | 7/2000 | Masaki et al. | |
| 6,146,494 A | 11/2000 | Seger et al. | |
| 6,231,557 B1 | 5/2001 | Krautkramer et al. | |
| 6,361,651 B1 | 3/2002 | Sun | |
| 6,471,824 B1 | 10/2002 | Jewell | |
| 6,506,282 B2 | 1/2003 | Hu et al. | |
| 6,579,414 B2 | 6/2003 | Jewell | |
| 6,579,415 B2 | 6/2003 | Jewell | |
| 6,582,557 B2 | 6/2003 | Jewell | |
| 6,592,712 B2 | 7/2003 | Koukoulas et al. | |
| 6,592,717 B2 | 7/2003 | Jewell | |
| 8,535,482 B2 * | 9/2013 | Jiang | D21C 9/001 162/164.1 |
| 8,871,059 B2 * | 10/2014 | Jaakkola | D21F 1/08 162/208 |
| 9,260,820 B2 * | 2/2016 | Sealey | D21H 17/66 |
| 9,347,182 B2 * | 5/2016 | Jaakkola | D21F 1/08 |
| 9,370,764 B2 * | 6/2016 | Tan | A61K 47/38 |
| 9,869,059 B2 * | 1/2018 | Sealey | D04H 1/732 |
| 9,909,257 B2 * | 3/2018 | Nonni | D21C 9/002 |
| 2002/0164914 A1 | 11/2002 | Qin et al. | |
| 2003/0024661 A1 | 2/2003 | Shore et al. | |
| 2003/0089453 A1 | 5/2003 | Tomsovic et al. | |
| 2003/0111168 A1 | 6/2003 | Olson et al. | |
| 2003/0115660 A1 | 6/2003 | Hopkins | |
| 2003/0125695 A1 | 7/2003 | Dorschner | |
| 2003/0125703 A1 | 7/2003 | Popp et al. | |
| 2003/0125704 A1 | 7/2003 | Koele et al. | |
| 2003/0125705 A1 | 7/2003 | Ruman et al. | |
| 2003/0125706 A1 | 7/2003 | Popp et al. | |
| 2003/0125707 A1 | 7/2003 | Popp et al. | |
| 2003/0168614 A1 | 9/2003 | Vogt et al. | |
| 2003/0195485 A1 | 10/2003 | Rangachari et al. | |
| 2003/0225390 A1 | 12/2003 | Vogt et al. | |
| 2003/0226862 A1 | 12/2003 | Vogt et al. | |
| 2004/0007318 A1 | 1/2004 | Popp et al. | |
| 2004/0007328 A1 | 1/2004 | Popp et al. | |
| 2004/0020579 A1 | 2/2004 | Durrance et al. | |
| 2004/0028268 A1 | 2/2004 | Popp et al. | |
| 2004/0073181 A1 | 4/2004 | Wallajapet et al. | |
| 2004/0098791 A1 | 5/2004 | Faulks | |
| 2004/0102746 A1 | 5/2004 | Mortell et al. | |
| 2004/0107481 A1 | 6/2004 | Mortell et al. | |
| 2004/0116881 A1 | 6/2004 | Nordness et al. | |
| 2004/0116889 A1 | 6/2004 | Carbone, II et al. | |
| 2004/0122394 A1 | 6/2004 | Fell et al. | |
| 2004/0144507 A1 | 7/2004 | Shannon et al. | |
| 2004/0216830 A1 | 11/2004 | Van Eperen | |
| 2004/0254549 A1 | 12/2004 | Olson et al. | |
| 2005/0008830 A1 | 1/2005 | Larson et al. | |
| 2005/0085784 A1 | 4/2005 | LeMinh et al. | |
| 2005/0096615 A1 | 5/2005 | Kuen et al. | |
| 2005/0112338 A1 | 5/2005 | Faulks et al. | |
| 2005/0125879 A1 | 6/2005 | Yang et al. | |
| 2005/0131377 A1 | 6/2005 | Franke et al. | |
| 2005/0131381 A1 | 6/2005 | Kuen et al. | |
| 2005/0131382 A1 | 6/2005 | Brud et al. | |
| 2005/0133150 A1 | 6/2005 | VanEperen et al. | |
| 2005/0133401 A1 | 6/2005 | Lange | |
| 2005/0136265 A1 | 6/2005 | Liu et al. | |
| 2005/0137547 A1 * | 6/2005 | Didier Garnier | A61F 13/15203 604/375 |
| 2005/0145150 A1 | 7/2005 | Mortell et al. | |
| 2005/0148961 A1 | 7/2005 | Sosalla et al. | |
| 2005/0148980 A1 | 7/2005 | Fitton | |
| 2005/0228349 A1 | 10/2005 | Long et al. | |
| 2005/0241748 A1 | 11/2005 | Allen | |
| 2006/0118258 A1 | 6/2006 | Chmielewski et al. | |
| 2006/0149210 A1 | 7/2006 | Sawyer et al. | |
| 2006/0243378 A1 | 11/2006 | Alberts | |
| 2006/0247599 A1 | 11/2006 | Mullen et al. | |
| 2007/0044608 A1 | 3/2007 | Franke | |
| 2007/0107862 A1 | 5/2007 | West et al. | |
| 2008/0294132 A1 * | 11/2008 | Tan | A61K 47/38 604/360 |
| 2010/0243186 A1 | 9/2010 | Bouplon et al. | |
| 2011/0030908 A1 * | 2/2011 | Sealey | D21H 17/66 162/162 |
| 2011/0034891 A1 * | 2/2011 | Jiang | D21C 9/001 604/358 |
| 2011/0108227 A1 * | 5/2011 | Sealey | D21C 9/001 162/181.9 |
| 2012/0048493 A1 * | 3/2012 | Sealey | D04H 1/425 162/179 |
| 2013/0139980 A1 | 6/2013 | Ban et al. | |
| 2013/0213594 A1 * | 8/2013 | Jaakkola | D21F 1/08 162/123 |
| 2014/0000827 A1 * | 1/2014 | Jiang | D21C 9/001 162/162 |
| 2014/0041817 A1 * | 2/2014 | Sealey | D04H 1/732 162/13 |
| 2014/0041818 A1 * | 2/2014 | Sealey | D21H 11/00 162/13 |
| 2014/0174681 A1 * | 6/2014 | Sealey | D21H 15/04 162/159 |
| 2015/0013926 A1 * | 1/2015 | Jaakkola | D21F 1/08 162/123 |
| 2015/0020987 A1 * | 1/2015 | Sealey | D04H 1/425 162/162 |
| 2015/0107792 A1 * | 4/2015 | Jiang | D21C 9/001 162/158 |
| 2016/0160445 A1 * | 6/2016 | Sealey | D21H 17/66 252/601 |

(56) References Cited

U.S. PATENT DOCUMENTS

| | | | |
|---|---|---|---|
| 2016/0237623 A1* | 8/2016 | Jaakkola | D21F 1/08 |
| 2016/0237624 A1* | 8/2016 | Jiang | D21C 9/001 |
| 2016/0289898 A1* | 10/2016 | Ramaratnam | D21H 27/008 |
| 2017/0081802 A1* | 3/2017 | Jaakkola | D21F 1/08 |
| 2017/0268178 A1* | 9/2017 | Ramaratnam | D21H 27/008 |
| 2017/0314207 A1* | 11/2017 | Sealey, II | D21H 27/30 |
| 2018/0058011 A1* | 3/2018 | Sealey | D21H 21/20 |
| 2018/0142414 A1* | 5/2018 | Sealey | D04H 1/732 |

FOREIGN PATENT DOCUMENTS

| | | | |
|---|---|---|---|
| CN | 1134271 | 10/1996 | |
| EP | 0339461 | 11/1989 | |
| EP | 0353334 | 2/1990 | |
| EP | 0410480 | 1/1991 | |
| EP | 0470594 | 2/1992 | |
| EP | 0532002 | 3/1993 | |
| EP | 0600454 | 6/1994 | |
| EP | 0601529 | 6/1994 | |
| GB | 2296512 | 7/1996 | |
| JP | 2015092034 A * | 5/2015 | C04B 18/241 |
| WO | WO-1991/11163 | 8/1991 | |
| WO | WO-1995/00703 | 1/1995 | |
| WO | WO-1999030751 | 6/1999 | |
| WO | WO-2000030582 | 6/2000 | |
| WO | WO-2000059438 | 10/2000 | |
| WO | WO-2001049230 | 7/2001 | |
| WO | WO-2001087206 | 11/2001 | |
| WO | WO-2001087217 | 11/2001 | |
| WO | WO-2001087218 | 11/2001 | |
| WO | WO-2001087561 | 11/2001 | |
| WO | WO-2001087562 | 11/2001 | |
| WO | WO-2001087752 | 11/2001 | |
| WO | WO-2001087753 | 11/2001 | |
| WO | WO-2006007226 | 1/2006 | |
| WO | WO-2007078537 | 7/2007 | |
| WO | WO-2011/017541 A2 | 2/2011 | |
| WO | WO-2012/018749 | 2/2012 | |
| WO | WO-2014026188 A1 * | 2/2014 | D04H 1/732 |

OTHER PUBLICATIONS

Technical Data Sheet—Pulp Business—Riegelwood, RW Supersoft Plus Fluff Pulp, Apr. 2012, 1 page.

* cited by examiner

FLUFF PULP AND HIGH SAP LOADED CORE

PRIORITY

This invention claims priority to U.S. Ser. No. 13/964,322, filed 12 Aug. 2013, now issued as U.S. Pat. No. 9,869,059, and U.S. Ser. No. 61/681,799, filed 10 Aug. 2012, said Applications are hereby incorporated herein in their entirety by the reference.

BACKGROUND

Field of the Invention

The invention relates to fluff pulp, processes for making, and uses thereof.

BRIEF DESCRIPTION OF THE FIGURES

Various embodiments are described in conjunction with the accompanying figures, in which.

DETAILED DESCRIPTION OF THE SEVERAL EMBODIMENTS

Figure 1:
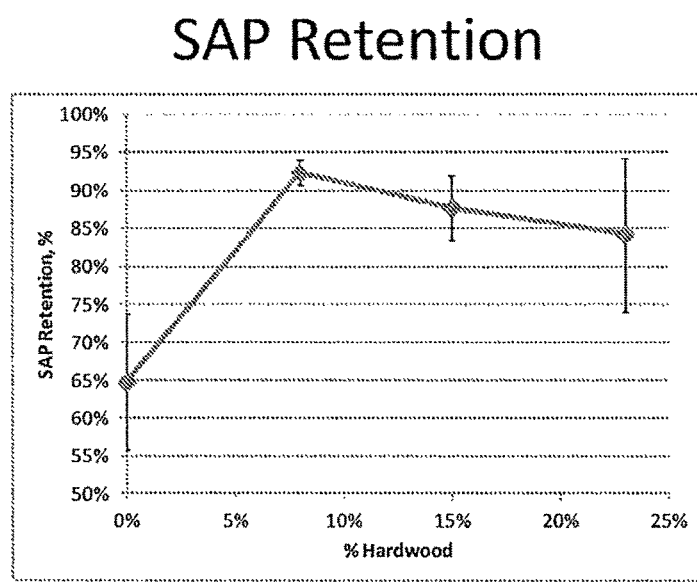
FIG. 1 shows SAP retention of exemplary and comparative embodiments.

One embodiment relates to fluff pulp, methods for making, and uses thereof. Another embodiment relates to fluff formed from the fluff pulp, methods for making, and uses thereof. Another embodiment relates to a core formed from the fluff, methods for making, and uses thereof. Another embodiment relates to products which include one or more of the fluff pulp, fluff, and/or core, methods for making, and uses thereof. Another embodiment relates to a thin core formed from the fluff, methods for making, and uses thereof. Another embodiment relates to a flexible core formed from the fluff, methods for making, and uses thereof. Another embodiment relates to an SAP (superabsorbent polymer) loaded core formed from the fluff and SAP particles, methods for making, and uses thereof. Another embodiment relates to a thin, high-SAP loaded core formed from the fluff, methods for making, and uses thereof. Another embodiment relates to the use of hardwood fiber and softwood fiber in a fluff pulp. Another embodiment relates to the use of hardwood fiber and softwood fiber and a simple sugar or slightly branched sugar in the fluff pulp or dried web. In one embodiment, the hardwood fiber will produce a thin core with low porosity to trap the SAP particles. In one embodiment, the short hardwood fibers limit the amount of fiber-fiber entanglement to make the core weaker when compressed to a very low caliper. In one embodiment, the sugar molecules can also prevent or inhibit strong bonding between fibers when compressed by providing a viscous fluid response. In one embodiment, prevention or inhibition of fiber-fiber bonding and/or fiber-fiber entanglement via one or both of the use of short hardwood fibers and sugar molecules allows the core to change shape with the body. In one embodiment, the sugar or sugar solution will help hold the SAP particles in the core due to the tacky or sticky properties of the sugar. In one embodiment, the core is flexible.

The inventors have investigated how to produce a thin and high SAP loaded core.

One embodiment relates to an absorbent core having improved SAP retention. Another embodiment relates to fluff pulp having good Mullen values. Another embodiment relates to a fluff pulp having reduced shred energy. Another embodiment relates to a fluff pulp having improved shred quality. Another embodiment relates to a fluff pulp having good shred absorption. Another embodiment relates to a fluff pulp having good rewet characteristics.

One embodiment relates to a fluff pulp, comprising softwood fibers; and 3 to 35% by weight of hardwood fibers.

One embodiment relates to a process for making fluff pulp, comprising contacting a first aqueous slurry comprising softwood fibers with a second aqueous slurry comprising hardwood fibers, to form a furnish; contacting the furnish onto a moving wire, to form a web; and drying and optionally pressing the web, to form the fluff pulp.

One embodiment relates to a fluff, comprising the fluff pulp in fiberized form.

One embodiment relates to a process for making fluff, comprising fiberizing the fluff pulp.

One embodiment relates to a core, comprising the fluff and one or more superabsorbent polymer (SAP).

One embodiment relates to a process for making a core, comprising contacting the fluff of and one or more superabsorbent polymer.

One embodiment relates to an absorbent product, paper product, personal care product, medical product, insulating product, construction product, structural material, cement, food product, veterinary product, packaging product, diaper, tampon, sanitary napkin, gauze, bandage, fire retardant, or a combination thereof, comprising the core and a supporting structure.

One embodiment relates to a process for making an absorbent product, comprising contacting at least a portion of the core with the supporting structure.

One embodiment relates to a process for making a fluff pulp, comprising foil ling a web comprising hardwood and softwood fibers, and drying, to produce a fluff pulp having softwood fibers and 3 to 35% by weight of hardwood fibers.

In one embodiment, the forming comprises one or more of contacting a fluff pulp mixture comprising fluff pulp fibers and water with a table in a papermaking machine, removing at least a portion of water from a fluff pulp mixture comprising fluff pulp fibers and water with a suction box under a table in a papermaking machine, at least partially drying a fluff pulp mixture comprising fluff pulp fibers and water in a flotation dryer, heating a fluff pulp mixture comprising fluff pulp fibers and water, or a combination thereof.

In embodiment, the web may be dried in a dryer, to form the dried web or fluff pulp. The web may be suitably dried in a drying section. Any method for drying commonly known in the art of fluff pulp papermaking may be utilized. The drying section may include a drying can, flotation dryer, cylinder drying, Condebelt drying, IR, or other drying means and mechanisms known in the art. The fluff pulp may be dried so as to contain any selected amount of water. In one embodiment, the web is dried using a flotation dryer.

As used herein, the term, "fluff pulp" may be used interchangeably with "dried web". Unless otherwise specified, the percent by weight or weight percent is based on the weight of the fluff pulp, fluff, or core as appropriate. As used herein, the term, "fluff" means fiberized or shredded fluff pulp, the terms, "fiberized" and "shredded" are used interchangeably herein, as is common in the art. As used herein, the term, "core" means a composition comprising fluff and at least SAP particles.

In one embodiment, the fluff pulp may have a basis weight ranging from 500 to 1100 gsm. This range includes all values and subranges therein, for example 500, 525, 550, 575, 600, 625, 650, 675, 700, 725, 750, 757, 775, 800, 825, 850, 875, 900, 950, 1000, 1150, and 1100 gsm, or any combination thereof or range therein.

In one embodiment, the fluff pulp has a moisture content of 15% by weight or less. This range includes all values and subranges therebetween, including 0, 0.1, 0.2, 0.3, 0.4, 0.5, 0.6, 0.7, 0.8, 0.9, 1, 2, 3, 4, 5, 6, 6.3, 7, 8, 8.5, 9, 10, 11, 12, 13, 14, and 15% by weight, or any combination thereof or range therein. In another embodiment, the fluff pulp has a moisture content of 20% or less. In another embodiment, the fluff pulp has a moisture content of 10% or less. In another embodiment, the fluff pulp has a moisture content of 6 to 9%. In another embodiment, the fluff pulp has a moisture content of about 6.3 to 8.5%. Moisture content may be suitably measured using TAPPI T 412 standard.

In one embodiment, the fluff pulp has a density of 0.5 to 0.75 g/cc. This range includes all values and subranges therebetween, including 0.5, 0.55, 0.6, 0.65, 0.7, and 0.75 g/cc, or any range therein.

In one embodiment, the fluff pulp has a caliper of 0.5-3 mm. This range includes all values and subranges therebetween, including 0.5, 0.6, 0.7, 0.8, 0.9, 1, 1.0, 1.1, 1.2, 1.3, 1.4, 1.5, 1.6, 1.7, 1.8, 1.9, 2, 2.1, 2.3, 2.5, 2.7, 2.9, and 3 mm, and any range therein. In one embodiment, the fluff pulp has a caliper of 1.1 to 1.5 mm. In one embodiment, the fluff pulp has a caliper of 1.3±0.2 mm.

The fiberization energy, sometimes called the shred energy, of the fluff pulp is not particularly limited. It may be suitably less than 170 kJ/kg. This range includes all values and subranges therebetween, including 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, and 170 kJ/kg, or any combination thereof or any range therein. In one embodiment, the fiberization energy of the fluff pulp is equal to or less than 160 kJ/kg. In another embodiment, the fiberization energy of the fluff pulp is from 100 to 160 kJ/kg. In another embodiment, the fiberization energy of the fluff pulp is from 120 to 160 kJ/kg.

In one embodiment, the fluff pulp has a Mullen of ≥90 psi. This range includes all values and subranges therebetween, including 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250 psi, and higher, or any range therein. Mullen may be easily determined according to TAPPI T 807.

In one embodiment, the fluff pulp further comprises one or more additive such as whitener, colorant, pigment, optical brightening agent, wetting agent, binder, bleaching agent, other additive, or a combination thereof. If present, the amount of additive is not particularly limited. In one embodiment, the additive may be present in amounts ranging from about 0.005 to about 50 by weight. This range includes all values and subranges therebetween, including about 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, and 50 weight percent, or any combination thereof, based on the weight of the fluff pulp mixture.

The fluff pulp may or may not include a debonder surfactant. In one embodiment, the fluff pulp includes one or more debonder surfactants. In another embodiment, the fluff pulp does not include a debonder surfactant. If present, the debonder surfactant may be present in an amount of ≥0.1 lb solids debonder surfactant per ton of fluff pulp. This range includes all values and subranges there between, including ≥0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.0, 2.1, 2.2, 2.3, 2.4, 2.5, 2.6, 2.7, 2.8, 2.9, 3, 3.0, 3.1, 3.2, 3.3, 3.4, 3.5, 3.6, 3.7, 3.8, 3.9, 4, 4.0, 5, 5.0, 6, 7, 8, 9, 10, 15, 20 lbs solids debonder surfactant per ton of the fluff pulp, and higher, or any combination thereof or any range therein. In one embodiment, if more than one debonder surfactant is used, this range is the total amount over all the debonder surfactants present in the fluff pulp.

In one embodiment, the finished fluff pulp may be fiberized or shredded, in accordance with methods known in the art. For example, the fiberizing or shredding may be carried out in a hammermill.

In one embodiment, the fluff pulp and/or fiberized or shredded fluff pulp, or core, or a combination thereof may be suitably incorporated into one or more of an absorbent product, paper product, personal care product, medical product, insulating product, construction product, structural material, cement, food product, veterinary product, packaging product, diaper, tampon, sanitary napkin, gauze, bandage, fire retardant, or a combination thereof. These products and methods for their manufacture and use are well known to those of ordinary skill in the art.

Another embodiment relates to a fluff pulp, made by the process described herein.

Another embodiment relates to an absorbent product, paper product, personal care product, medical product, insulating product, construction product, structural material, cement, food product, veterinary product, packaging product, diaper, tampon, sanitary napkin, gauze, bandage, fire retardant, or a combination thereof, comprising the fluff pulp and/or fiberized or shredded fluff pulp, or core, or a combination thereof.

Another embodiment relates to the use of an absorbent product, paper product, personal care product, medical product, insulating product, construction product, structural material, cement, food product, veterinary product, packaging product, diaper, tampon, sanitary napkin, gauze, bandage, fire retardant, or a combination thereof, comprising the fluff pulp and/or fiberized or shredded fluff pulp, or core, or a combination thereof.

One or more than one, or any combination thereof, of fibers may be used in the fluff pulp. The fibers may be treated or untreated, and they may optionally contain one or more than one additives, or combination thereof, which are known in the art. Given the teachings herein, the level of treatment, if desired, and the amount of additives may be readily determined by one of ordinary skill in the fluff pulp and fluff pulp fiber arts.

Similarly, the formation of a web of fluff pulp or fluff pulp fibers or from a fluff pulp mixture or furnish onto a table from a headbox in a papermaking machine is within the skill of one knowledgeable in the fluff pulp and fluff pulp fiber arts.

The type of fluff pulp or fluff pulp fiber suitable for use herein is not intended to be limiting. Fluff pulp typically includes cellulosic fiber. The type of cellulosic fiber in the fluff pulp is not critical. For example, the fluff pulp can be made from pulp fibers derived from hardwood trees, softwood trees, or a combination of hardwood and softwood trees. The fluff pulp may also include synthetic fibers, in addition to one or more types of cellulosic fibers. The fluff pulp fibers may be prepared by one or more known or suitable digestion, refining, and/or bleaching operations such as, for example, known mechanical, thermomechanical, chemical and/or semichemical pulping and/or other well known pulping processes. The term, "hardwood pulps" as may be used herein include fibrous pulp derived from the woody substance of deciduous trees (angiosperms) such as birch, oak, beech, maple, and eucalyptus. The term, "softwood pulps" as may be used herein include fibrous pulps derived from the woody substance of coniferous trees (gymnosperms) such as varieties of fir, spruce, and pine, as for example loblolly pine, slash pine, Colorado spruce, balsam fir and Douglas fir. In some embodiments, at least a portion of the pulp fibers may be provided from non-woody herbaceous plants including, but not limited to, kenaf, hemp, jute, flax, sisal, or abaca, although legal restrictions and other considerations may make the utilization of hemp and other fiber sources impractical or impossible. Either bleached or unbleached fluff pulp fiber may be utilized. Recycled fluff pulp fibers are also suitable for use. The fluff pulp may suitably contain from 30 to 100 wt % of fluff pulp fibers based upon the total weight of the fluff pulp. In one embodiment, the fluff pulp may contain from 30 to 99 wt % of fluff pulp fibers based upon the total weight of the fluff pulp. In another embodiment, the fluff pulp contains 40 to 95 wt % of fluff pulp fibers based upon the total weight of the fluff pulp. These ranges include any and all values and subranges therebetween, for example, 30, 35, 40, 45, 50, 55, 60, 65, 70, 75, 80, 85, 90, 91, 92, 93, 94, 95, 96, 97, 98, 99, and 100 wt % or any subrange therein, based upon the total weight of the fluff pulp.

The fluff pulp may optionally contain from 65 to 97 wt % fluff pulp fibers originating from softwood species based upon the total weight of the fluff pulp. In one embodiment, the fluff pulp may contain 70 to 94 wt % fluff pulp fibers originating from softwood species. These ranges include 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, and 97 wt % or any subrange therein, based upon the total weight of the fluff pulp.

All or part of the softwood fibers may optionally originate from softwood species having a Canadian Standard Freeness (CSF) of from 500 to 800. In one embodiment, the fluff pulp contains fluff pulp fibers from a softwood species having a CSF from 500 to 800. These ranges include any and all values and subranges therebetween, for example, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, and 800 CSF or any subrange therein. Canadian Standard Freeness is as measured by TAPPI T-227 standard test.

The fluff pulp may optionally contain from 3 to 35 wt % fluff pulp fibers originating from hardwood species. These ranges include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35 wt %, or any subrange therein, based upon the weight of the fluff pulp.

All or part of the hardwood fibers may optionally originate from hardwood species having a Canadian Standard Freeness of from 500 to 650. This range includes 500, 510, 520, 530, 540, 550, 560, 570, 580, 590, 600, 610, 620, 630, 640, and 650 CSF, or any subrange therein.

In one embodiment, where only hardwood and softwood fibers are present in the fluff pulp, the hardwood/softwood fluff pulp fiber weight ratio may range from 3/97 to 35/65. These ranges include all values and subranges therebetween, including 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35 (for hardwood) to 100 minus the aforementioned values (for softwood).

The softwood fibers, hardwood fibers, or both may be optionally modified by physical and/or chemical processes to obtain the fluff pulp. Examples of physical processes include, but are not limited to, electromagnetic and mechanical processes. Examples of electrical modifications include, but are not limited to, processes involving contacting the fibers with an electromagnetic energy source such as light and/or electrical current. Examples of mechanical modifications include, but are not limited to, processes involving contacting an inanimate object with the fibers. Examples of such inanimate objects include those with sharp and/or dull edges. Such processes also involve, for example, cutting, kneading, pounding, impaling, and the like, and combinations thereof.

If present, the synthetic fibers are not particularly limiting. Non-limiting examples of such fibers include polyethylene, polypropylene, polyvinyl alcohol, core/sheath fibers, bi-component fibers, bi-component or core/sheath fibers of polyethylene and polypropylene. Combinations of different synthetic fibers are possible.

A simple sugar or slightly branched sugar may optionally be present in the fluff pulp, fluff, or core. Nonlimiting examples include sucrose, fructose, dextrose, hexose, L-arabinose, oligosaccharide, monosaccharide, disaccharide, glucose, galactose, maltose, lactose, sugar pulp, bagasse, sugar cane pulp, sugar beet pulp, or combination thereof. If present, the sugar may be present in an amount ranging from 1 to 40% by weight, which range includes all values and subranges therebetween, including 1, 5, 10, 15, 20, 25, 30, 35, and 40% by weight or any combination thereof or subrange therein. The sugar, if desired, may be added at any point during the making of fluff pulp, fluff, and/or core. In one embodiment, the sugar may be contacted with the fluff pulp before, during, or after an airlaid process, or a combination thereof.

Nonlimiting examples of chemical modifications include conventional chemical fiber processes such as bleaching, crosslinking and/or precipitation of complexes thereon. Other examples of suitable modifications of fibers include those found in U.S. Pat. Nos. 6,592,717, 6,592,712, 6,582, 557, 6,579,415, 6,579,414, 6,506,282, 6,471,824, 6,361,651, 6,146,494, H1,704, 5,731,080, 5,698,688, 5,698,074, 5,667, 637, 5,662,773, 5,531,728, 5,443,899, 5,360,420, 5,266,250, 5,209,953, 5,160,789, 5,049,235, 4,986,882, 4,496,427, 4,431,481, 4,174,417, 4,166,894, 4,075,136, and 4,022,965, the entire contents of each of which are hereby incorporated, independently, by reference.

As discussed herein, if desired, additives such as pH adjusting agent, whitener, colorant, pigment, optical brightening agent, wetting agent, binder, bleaching agent, trivalent cationic metal, alum, other additive, or a combination thereof may be utilized. Such compounds are known in the art and otherwise commercially available. Given the teachings herein, one of ordinary skill in the fluff pulp and fluff pulp papermaking arts would be able to select and use them as appropriate. If present, the amount of additive is not particularly limited. In one embodiment, the additive may be present in amounts ranging from about 0.005 to about 20 weight percent based on the weight of the fluff pulp. This range includes all values and subranges therebetween, including about 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, and 20 weight percent, or any combination thereof or subrange therein, based on the weight of the finished fluff pulp.

One or more optical brightening agents may be optionally present. Typically, the optical brightening agents are fluorescent dyes or pigments that absorb ultraviolet radiation and reemit it at a higher wavelength in the visible spectrum (blue), thereby effecting a white, bright appearance to the fluff pulp, but any optical brightening agent may be used. Examples of optical brighteners include, but are not limited to azoles, biphenyls, coumarins, furans, stilbenes, ionic brighteners, including anionic, cationic, and anionic (neutral) compounds, such as the Eccobrite™ and Eccowhite™ compounds available from Eastern Color & Chemical Co. (Providence, R.I.); naphthalimides; pyrazenes; substituted (e.g., sulfonated) stilbenes, such as the Leucophor™ range of optical brighteners available from the Clariant Corporation (Muttenz, Switzerland), and Tinopal™ from Ciba Specialty Chemicals (Basel, Switzerland); salts of such compounds including but not limited to alkali metal salts, alkaline earth metal salts, transition metal salts, organic salts and ammonium salts of such brightening agents; and combinations of one or more of the foregoing agents.

Examples of optional fillers include, but are not limited to, clay, calcium carbonate, calcium sulfate hemihydrate, and calcium sulfate dehydrate, chalk, GCC, PCC, and the like.

Examples of optional binders include, but are not limited to, polyvinyl alcohol, Amres (a Kymene type), Bayer Parez, polychloride emulsion, modified starch such as hydroxyethyl starch, starch, polyacrylamide, modified polyacrylamide, polyol, polyol carbonyl adduct, ethanedial/polyol condensate, polyamide, epichlorohydrin, glyoxal, glyoxal urea, ethanedial, aliphatic polyisocyanate, isocyanate, 1,6 hexamethylene diisocyanate, diisocyanate, polyisocyanate, polyester, polyester resin, polyacrylate, polyacrylate resin, acrylate, and methacrylate. Other optional substances include, but are not limited to silicas such as colloids and/or sols. Examples of silicas include, but are not limited to, sodium silicate and/or borosilicates.

The composition may optionally and additionally include one or more pigments. Non-limiting examples of pigments include calcium carbonate, kaolin clay, calcined clay, aluminum trihydrate, titanium dioxide, talc, plastic pigment, ground calcium carbonate, precipitated calcium carbonate, amorphous silica, modified calcium carbonate, modified calcined clay, aluminum silicate, zeolite, aluminum oxide, colloidal silica, colloidal alumina slurry, modified calcium carbonate, modified ground calcium carbonate, modified precipitated calcium carbonate, or a mixture thereof.

The fluff pulp fibers may be formed into a single or multi-ply web on a papermaking machine such as a Fourdrinier machine or any other suitable papermaking machine known in the art. The basic methodologies involved in making fluff pulps on various papermaking machine configurations are well known to those of ordinary skill in the art and accordingly will not be described in detail herein. In one embodiment, one or more of the fluff pulp furnish, hardwood slurry, and softwood slurry may have the form of a relatively low consistency aqueous slurry of the pulp fibers optionally together with one or more additives. In one embodiment, the fluff pulp furnish is ejected from a head box onto a table, e.g., a porous endless moving forming sheet or wire, where the liquid, e.g., water, is gradually drained through small openings in the wire, optionally with the aid of one or more suction boxes, until a mat of pulp fibers and optionally the other materials is formed on the wire. In one embodiment, the still-wet web is transferred from the wire to a wet press where more fiber-to-fiber consolidation occurs and the moisture is further decreased. In one embodiment, the web is then passed to a dryer section to remove a portion of, most of, or substantially all of the retained moisture and further consolidate the fibers in the web. After drying, the dried web or fluff pulp may be further treated with a formation shower, spray boom, or the like.

If desired, the fluff pulp may be rolled onto a roll, to form a roll of fluff pulp, or it may be cut into sheets, and stacked, to form a bale of the fluff pulp. Alternatively, the (wet) web may be sent to a flash dryer or similar, and dried therein, and thereafter bagged, to form a bag containing the fluff pulp.

The fluff pulp, once obtained, may be fiberized or shredded to produce fluff. Fluff includes the fluff pulp in fiberized form.

In one embodiment, the fluff has a multi-dose rewet value of 3 to 8 grams for the second and third dose. This range includes all values and subranges therebetween, including 3, 3.5, 4, 4.5, 5, 5.25, 5.5, 5.75, 6, 6.25, 6.5, 6.75, 7, 7.5, and 8 grams.

In one embodiment, the fluff has a SCAN-C 33:80 adsorption time of <4.0 s. This range includes all values and subranges therebetween, including 1, 1.1, 1.2, 1.3, 1.4, 1.5, 1.6, 1.7, 1.8, 1.9, 2, 2.0, 2.1, 2.2., 2.3, 2.4, 2.5, 2.6, 2.7, 2.8, 2.9, 3, 3.0, 3.1, 3.2, 3.3, 3.4, 3.5, 3.6, 3.7, 3.8, 3.9, <4.0 s, or any range therein.

In one embodiment, the fluff has an absorptive capacity of 4 to 10 g/g. This range includes all values and subranges therebetween, including 4, 4.5, 5, 5.5, 6, 6.5, 7, 7.5, 8, 8.5, 9, 9.5, and 10 g/g, or any range therein. Absorptive capacity, sometimes called shred absorption, may be suitably measured using the Scan Absorption Test described herein.

In one embodiment, the fluff on screen fractionation has a % Good of ≥50%. This range includes all values and subranges therebetween, including 50, 55, 60, 65, 70, 75, 80, 85, 90, 95, 100%, or any range therein.

In one embodiment, the fluff on screen fractionation has a % Fines of ≤40%. This range includes all values and subranges therebetween, including 1, 2, 3, 4, 5, 6, 7, 8, 9, 10, 15, 20, 25, 30, 35, 40%, or any combination thereof or any range therein.

In one embodiment, the fluff on screen fractionation has a % Pieces of ≤30%. This range includes all values and subranges therebetween, including 1, 2, 3, 4, 5, 6, 7, 8, 9, 10, 15, 20, 25, 30%, or any combination thereof or any range therein.

One embodiment relates to a core, comprising the fluff and one or more superabsorbent polymer (SAP).

One embodiment relates to a process for making a core, comprising contacting the fluff of and one or more superabsorbent polymer.

In the course of making the core, the fluff may be combined with one or more superabsorbent polymers (SAP). SAPs are known in the absorbent product art, and are not particularly limited. Nonlimiting examples of SAPs include starch-acrylonitrile copolymer, hydrolyzed starch-acrylonitrile copolymer, acrylic acid (co)polymer, acrylamide (co)polymer, polyvinyl alcohol, polyacrylate/polyacrylamide copolymers, polyacrylic acid (co)polymers, sodium polyacrylate, ethylene maleic anhydride copolymer, cross-linked carboxymethylcellulose, polyvinyl alcohol copolymer, polyethylene oxide, cross-linked polyethylene oxide, and starch grafted copolymer of polyacrylonitrile, salts thereof, and combination thereof.

The amount of SAP in the core is not particularly limited, and may suitably range from 1 to 95% by weight of the core. This range includes all values and subranges therebetween, including 1, 5, 10, 15, 20, 25, 30, 35, 40, 45, 50, 55, 60, 65, 70, 75, 80, 85, 90, and 95% by weight of the core. In one embodiment, a "high" amount of SAP load is ≥50% by weight of the core.

The SAP may suitably be contacted with the fluff during an airlaid process, in the course of making the core.

In one embodiment, the core has a caliper of 2 to 500 mm. This range includes all values and subranges therebetween, including 2, 3, 4, 5, 6, 7, 8, 9, 10, 15, 20, 25, 50, 75, 100, 150, 200, 250, 300, 400, and 500, and any range therein. In one embodiment, the core has a caliper of 2 to 50 mm. In one embodiment, a "thin" caliper for the core is 2 to 25 mm.

In one embodiment, porosity is related to the bulk of the core. In one embodiment, higher porosity is associated with a higher bulk; and a lower porosity is associated with a lower bulk. The unit of measurement for porosity is seconds, which is the length of time required for a given amount of air to pass through a sample. A higher porosity sample will allow a given amount of air to pass through more quickly than would a lower porosity sample. In one embodiment, a higher proportion of hardwood results in a higher density and also a lower porosity. For example, typical bulk values of 1 1-5 cc/g are observed for most papers, and 6 cc/g would be considered high.

In one embodiment, the core may have a bulk value of 2 to 6 cc/g. This range includes all values and subranges therebetween, including 2, 3, 4, 5, 6 cc/g, or any subrange therein.

In one embodiment, the core can be produced in an airlaid process. This can involve one or more steps of fiber defibration, web formation, web bonding, or a combination of two or more thereof.

In fiber defibration, the fluff pulp or dried web may be fed into one or more hammermills, saw mills, and/or pin mills, or any combination thereof. They may have a series of series of saws, or pins, or small hammers, for example, that rotate at high speed separating the pulp into individual loose fibers. The fibers are then transported to the web forming system. Synthetic fibers, natural fibers, or both synthetic and natural fibers can also be added at this stage. These may arrive in compact bale form and fed into bale opening systems which loosen and separate the bales into individual fibers.

In web formation, any known forming technologies may be used to produce airlaid webs of fluff In one embodiment, the fiberized fluff pulp fibers are sifted through a coarse screen and deposited with vacuum assistance onto a forming wire below. In another embodiment, drum formers may be used, wherein fibers pass through a series of holes or slots in a large cylinder that spans the width of the forming wire. In one embodiment, the fluff web is kept in place by a vacuum system located below the forming wire, and additives, such as superabsorbent polymers or odor control powders, can be incorporated into the web at this stage.

More than one web former may be utilized to allow for flexibility in the web formation and increase line throughput. The technology often allows for the web composition and structure to be controlled to achieve various required functions. Prior to bonding, the web may be compacted by large rollers to provide some integrity and cohesiveness. It can also be embossed with a design or logo as required by the customer.

For bonding and web consolidation, any method may be used as desired. For example, latex, thermal and/or hydrogen bonding may be utilized. In one embodiment, multi-bonding, wherein more than one bonding method is used in combination. In one embodiment, latex and thermal bonding may be used in combination. Other combinations are possible.

Latex bonding may be utilized to bond the web, wherein latex binder is contacted with the web. In one embodiment, the top of the compacted web is sprayed with latex, and dried in an oven; and then the web is flipped over so that it can be sprayed on the other side. It then goes through a second oven that dries and cures the binder before the web is cooled, slit and wound into rolls. In another embodiment, a latex foam is utilized instead of a spray.

In thermal bonding, synthetic bonding fibers are present. In one embodiment, the synthetic bonding fibers include bi-component fibers with polyethylene and polypropylene. In one embodiment, after compaction the web is transported into an oven which softens and melts the sheaths of the fibers such that they fuse together and bond the various components of the web. The web may then be calendered if desired to the correct thickness, cooled and transported to the slitting/rewinding system.

In hydrogen-bonding, cellulose fibers bond together when naturally occurring moisture contained in the fibers is removed while the fibers are in close contact. This may be suitably carried out under conditions of high temperature and pressure. Synthetic binders may be added to the airlaid web or eliminated from the airlaid web.

In one embodiment of multi-bonding, a combination of latex and thermal bonding is used; the web is thermally bonded, and latex is sprayed on both sides of the web, if desired, to reduce the lint that is often released in high-speed converting operations.

The fluff or core may be suitably used in an absorbent product, paper product, personal care product, medical product, insulating product, construction product, structural material, cement, food product, veterinary product, packaging product, diaper, tampon, sanitary napkin, gauze, bandage, fire retardant, or a combination thereof, comprising the fluff pulp and/or fiberized or shredded fluff pulp, or core, or a combination thereof. These products typically include the fluff or core (as a whole or a part of the absorptive portion) and one or more supporting structures or materials.

For example, a supporting structure or material may include one or more non-woven, non-woven layer, non-woven top sheet, wicking layer, film, back sheet, moisture barrier, non-porous layer, acquisition distribution layer, or the like, or combination thereof. The supporting structure or material may or may not provide a supporting function to the core; for example, it may simply contain the core, or provide a barrier between the user and the core, or between the core and the environment. A feminine hygiene pad may include the core and a non-woven and/or wicking layer between the core and the skin of the user; and a back sheet or moisture barrier on the backside thereof to mitigate or prevent fluid loss or staining; and optionally one or more wings, adhesive strip, deodorant, and the like. A tampon may include the core, non-woven or wicking material between the core and the user; a string for removal, and optionally an insertion device including a barrel, grip, plunger, or similar. A diaper may include the core and a non-woven layer, wicking layer, or the like, and a non-porous outer layer, such as a polypropylene or polyethylene outer layer. A medical product may include the core and a non-woven or wicking layer between the core and the user, and a backing optionally non-porous layer. A bandage can further include an adhesive layer to adhere the bandage containing the core to the skin. An oil boom might include a mesh or porous layer surrounding all or a portion of the core. Such supporting structures are known in the art. Given the teachings herein, combined with the knowledge of one of the ordinary skill in the relevant art, one could easily produce an absorptive product comprising at least the core and the supporting structure.

Shred Energy Procedure. For fluff pulp shredding, the Kamas hammermill is a simulation of commercial equipment manufactured and supplied by Kamas Industri AB for use in the production of fluff pulp products. Like the commercial equipment it has variable rotor speed, variable pulp feed speed and exchangeable screens. Pulp strips are hand fed into the mill and are defiberized with free swinging hammers until the resultant fluff is sufficiently broken up to pass through the screen holes. In the fluff testing room, controlled conditions, 72° F. and 55% (+/−5) relative humidity are used; and for apparatus, a Kamas Type H 01 Laboratory Defribrator was used. Samples were prepared by conditioning pulp sheets in the testing room for at least 4 hours. For lab formed sheets, trim about ½" from edges. Cut pulp sheets (in machine direction) into strips, 5-10 strips/ sample, 2 inches wide. Record weights. Air flow when running should be 32.5-35 L/sec.; Set rotor to 3300 rpm, feed to ~15 cm/sec, time to 7 seconds, and use 10 mm screen unless otherwise specified; Feed in the next sample strip and repeat; Collect the shredded pulp in the screen receptor funnel; Empty fluff into plastic bag; Mix by hand, then seal bag and shake vigorously to get a homogenous fluff mix.

Shred Quality: Four Screen Fractionation of Shredded Fluff Pulp test can determine the size distribution of fibers in dry shredded pulp. A moving high velocity air stream disperses shredded pulp in a covered standard testing sieve while individual fibers are removed through the wire mesh by an applied vacuum. The amount of fluff retained on the sieve wire is determined by weight. The fiber is subjected to fractionation through a series of sieves with consecutively increasing hole openings. The fractions are calculated as a percentage of the original whole fluff weight. The apparatus includes pulp fluff air turbulence generator and separator; USA Standard Testing Sieves: 8" diameter×2" height; USA Std #200 (75 µm hole opening); USA Std #50 (300 µm hole opening); USA Std #14 (1400 µm hole opening); USA Std #8 (2360 µm hole opening. This test must be conducted in a controlled room, 48% to 52% relative humidity, 70° F. to 72° F.

Procedure: (1) Condition shredded pulp at least 4 hrs in the test room. Mix the fluff in the plastic bag by hand and by vigorously shaking the sealed bag which contains air space, to achieve a uniform a distribution of fiber fractions and to achieve a representative test sample. (2) Take pulp from various areas of the bag, and weigh out 5 grams (+/−0.01 grams). Record weight, and place on a tared #200 sieve. Place sieve on the fluff fractionator and cover. Seal the seam formed by the sieve with the large rubber gasket to allow a more uniform distribution of the air/vacuum. (3) Set timer for 5 minutes and start fractionator. Adjust compressed air to 30 psi and vacuum to 4 inches. The fines will pass through the sieve into the vacuum. When finished, remove the sieve, remove the cover and weigh the sieve plus the pulp on the tared balance. Record the weight of pulp remaining on the #200 sieve. The mass of the fines is the difference in the mass of the pulp before and after fractionation. (4) Tare the #50 sieve and transfer the pulp from step 3 on to the #50 sieve, cover, place on fractionator and seal. Set timer for 5 minutes; Start fractionator and proceed as in step 3 (adjust air and vacuum as needed). Record the weight of the pulp retained on the #50 screen. (5) Tare the #14 sieve and transfer the pulp from the #50 on to the #14 sieve, cover, place on fractionator and seal as in step 2. Set timer for 5 minutes. Reset the start by turning the knob to off, then back to auto. Start fractionator and proceed as in step 3 (adjust air and vacuum as needed). Record weight of the pulp retained on the #14 screen. (6) Transfer the pulp from the #14 to the #8 screen. Repeat the process above (5 minutes, 30 psi, vacuum at 4 in.) and record the weight of pulp retained on the #8. Calculations: For the calculations, (1) Original fluff weight; (2) Weight remaining on #200; (3) Weight remaining on #50; (4) Weight remaining on #14; and (5) Weight remaining on #8. Percent passing #200={(1)−(2)}/(1)× 100=% Fines. Percent retained on #200={(2)−(3)}/(1)× 100=% Good. Percent retained on #50={(3)−(4)}/(1) ×100=% Good. Percent retained on #14={(4)−(5)}/(1)× 100=% Nits (fiber agglomerates). Percent retained on #8= (5)/(1)×100=% Pieces. Percent passing #200 is reported as Fines. Percent retained on #200 screen, but passing #50 is reported as Good. Percent retained on #50, but passing #14 is reported as Good. (Total Good is sum of the two good fractions). Percent retained on #14 screen, but passing #8 screen is reported as Nits (fiber agglomerates). Percent retained on #8 screen is reported as Pieces. It is recommended to run a minimum of three tests per sample.

Scan Absorption Test can determine absorption properties (Shred Absorption, sometimes called Absorption Capacity) of fluff pulp pads. The method is based on the Scandinavian standard SCAN-C 33:80, the entire contents of which are hereby incorporated by reference. Fluff volume (bulk), absorption rate and absorption capacity are measured by placing a test pad on the unit, applying a uniform load and allowing the pad to absorb liquid from below until saturated. The apparatus is a SCAN Absorption Tester, which includes a test piece former, absorption unit, and timing device. Reagents include 0.9% saline (NaCl) solution. Procedure: (1) Prepare saline solution, 0.9% sodium chloride in DI water (e.g., 180 g/20 L) and transfer to saline delivery carboy; (2) Rinse electrode platen and blot dry with wipe; rinse screen and reservoir to remove residue, dry and replace in tester. Open valve on carboy and run saline through until it flows into overflow pail; Close valve; If necessary, stabilize the instrument by running a few samples before analyzing test samples; (3) Mix fluff by vigorously shaking inflated sample bag; Weigh out approximately 3.20 g of fluff pulp (take several small portions throughout the bag to get a representative sample); (4) Tare the forming tube (the plexiglass cylindrical mold with 50 mm base screen) and place securely on pad former (make sure it's firmly seated on gasket); Turn on vacuum and feed the pulp into the former in small amounts, allowing fibers to separate as much as possible; Avoid feeding in clumps of pulp; (5) After pad has been formed turn off vacuum and remove mold/screen assembly; Place tared assembly with pad on balance and remove excess pulp to give a final weight of 3.00 g +/−0.01; Arrange pulp as needed to give uniform thickness; Fibers sometimes build up on one side in tube, especially if high in nits; Remove from this area first to get the 3.00 g, then rearrange as needed, carefully lifting mat/fibers to the thinner area; Gently tamp down the moved fibers to give a uniform thickness; Prepare 6-8 pads per sample; (6) Sample wt 3.00 g; (7) Pre-wet the SCAN tester sample basket and use wipe to remove excess; Lower the electrode platen and zero height sensor; Raise and latch the electrode platen; (8) Remove bottom screen from forming tube; Place plexi tube on the SCAN wire basket; gently lower the electrode platen (with the load on top of shaft) onto the pad; carefully raise the mold (hold in place); start timer then swing holder over and rest the tube on it; Avoid touching the wires and shaft with the tube; start the saline flow at about 18-20 seconds; at 30 sec, raise the reservoir in one even motion, and hold in place; When prompted, lower the reservoir, close the saline valve and allow pad to drain; When prompted, raise the electrode platen up through the former tube; If pad sticks to the platen, gently tap with edge of tube to release pad onto the basket; Latch the electrode platen, remove forming tube and carefully transfer pad to a balance; Record wet weight; Enter wet pad weight in computer; Record the dry height (caliper, mm), specific volume (cc/g), absorption time (sec) and wet weight on spreadsheet; Report absorption time (sec), absorption rate (cm/sec), specific volume (glee), and capacity (g/g); Run 6-10 tests per sample; Report averages and SD.

Multi-Dose Acquisition Test Procedure: A 5"×12" air laid shredded fluff pulp sample is compressed to a density of 0.15 gms/cm$^3$; A sheet of coverstock is placed on top of the compressed sample; A 1" diameter dosing tube weighing 1000 g is centered on top of the sample; 30 mls of 0.9% saline solution is dosed at a flow rate of 7 mls/sec; Timing begins once the dosage started and ended when all of the saline solution is absorbed and the absorption time is recorded; After 300 seconds after the first dose is absorbed a second dose of saline solution is applied and the timing procedure is repeated and the absorption time recorded; 300 seconds after the second dose is absorbed a third dose is applied and the timing procedure is repeated and the absorption time recorded.

Multi-Dose Rewet Test Procedure/Two Dose Rewet: A 5"×12" air laid shredded fluff pulp sample is compressed to a density of 0.15 gms/cm$^3$; A sheet of coverstock is placed on top of the compressed sample; A 1" diameter dosing tube weighing 1000 g is centered on top of the sample; 30 mls. of 0.9% saline solution was dosed at a flow rate of 7 mls/sec; After 300 seconds a second dose of saline solution is applied; 300 seconds after the second dose the dosing tube is removed and a recorded preweighed 8"×8" sheet of Verigood blotter paper is placed on top and a 50 cm2 3 kpa load is applied for 60 seconds; The load is removed and the blotter paper is weighed. The difference between the wet and dry paper is recorded as rewet.

SAP Retention Procedure: Produce fluffed pulp by fiberizing sheets in a Kamas H 01 hammermill at specified conditions. Form 1.9 g pads as follows: Insert 14 mm screen in hammermill. Set the rotor to ~800 rpm. Place a carrier piece of non-woven material on the 50 in$^2$ forming screen and secure screen to funnel and install in vacuum chamber. Weigh out ~1.9 g fluffed pulp in a weighing dish. Weigh out the desired % SAP for the test. Sprinkle the SAP evenly over the fluff Start the rotor and feed all the pulp at once into the shredder through the front chute. Stop the rotor and remove the funnel apparatus from bottom chamber. Use a tamping device to compress pulp onto the forming screen. Remove top funnel. Remove pad and non-woven carrier together. Fold the non-woven over the top of pad. Place the press ring on the nylon block. Put the pad inside ring bottom down and place the rod inside ring. Put 1000 g weight on rod and place in carver press. Press to 1000 psi and release pressure. Set sonic sifter at a 2 amplitude. Prepare the sieve stack with the 60 mesh screen on top and 400 mesh screen on bottom. Remove pad from non-woven and place on 60 mesh sieve. Place stack into sifter. Set timer to three minutes and press start. Collect and weigh SAP from the non-woven, 60 and 400 sieves. Calculate SAP retained.

EXAMPLES

Four fluff pulps were prepared on a paper machine as described herein, which contained different levels of hardwood fiber. The four fluff pulps contained 0%, 8%, 15%, and 23% by weight hardwood fibers. These fluff pulps were characterized for their fluff pulp properties as well as fluff quality as described within. The ability to retain SAP in a densified air laid core of fluff pulp was also measured, as described herein.

FIG. 1 shows SAP retention of exemplary and comparative embodiments. The procedure included forming a pad with 50% fluff pulp and 50% SAP. The pad was then shaken on a mesh screen. The SAP weight % retained was then determined by the difference between before and after shaking.

Figure 2:
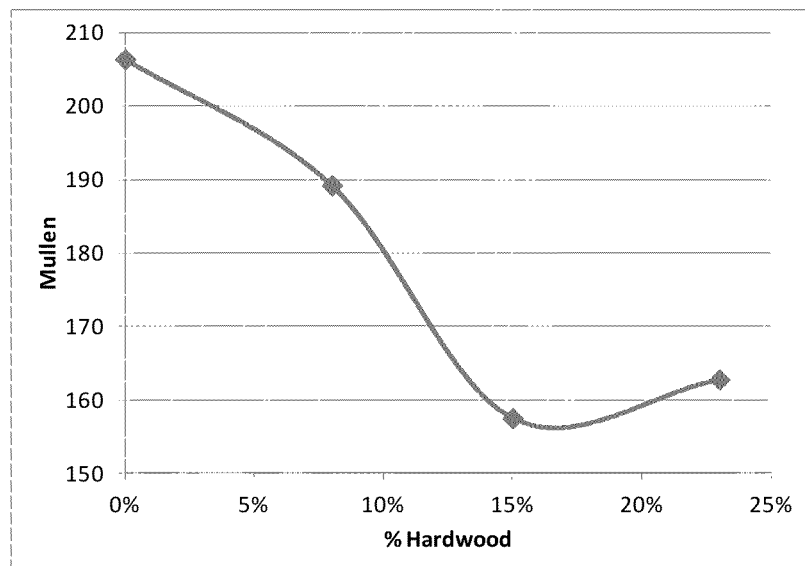
FIG. 2 shows mullen values of exemplary and comparative embodiments.

FIG. 2 shows mullen values of exemplary and comparative embodiments.

Figure 3:
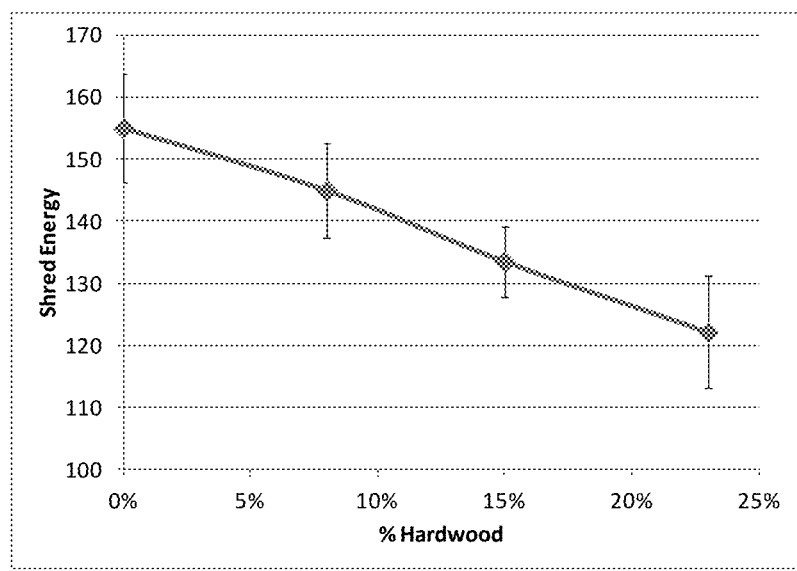
FIG. 3 shows shred energy values of exemplary and comparative embodiments.

FIG. 3 shows shred energy values of exemplary and comparative embodiments.

Figure 4:
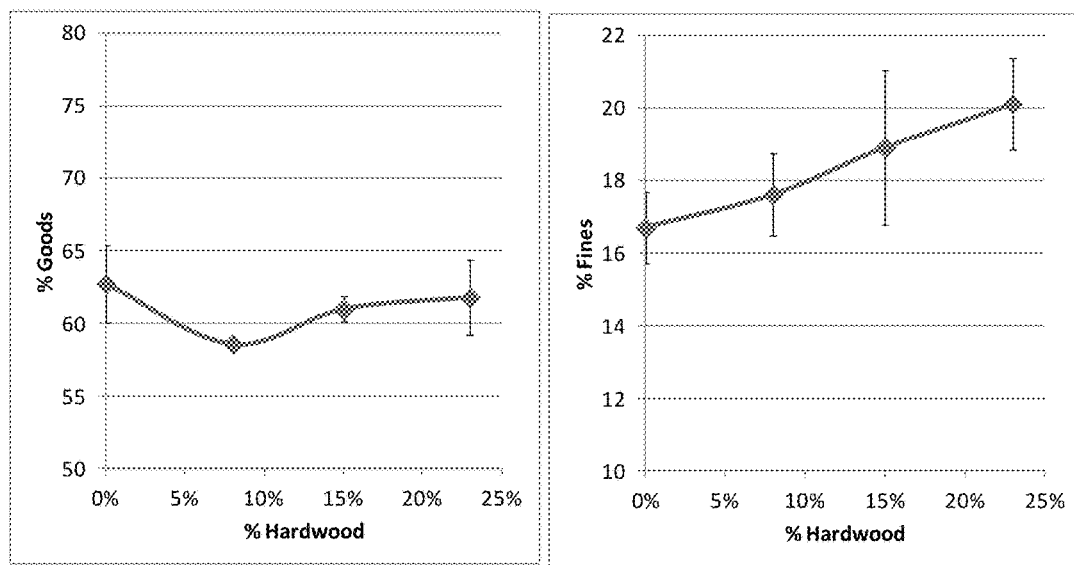
FIG. 4 shows shred quality in percent goods and fines for exemplary and comparative embodiments.

FIG. 4 shows shred quality in percent goods and fines for exemplary and comparative embodiments.

Figure 5:
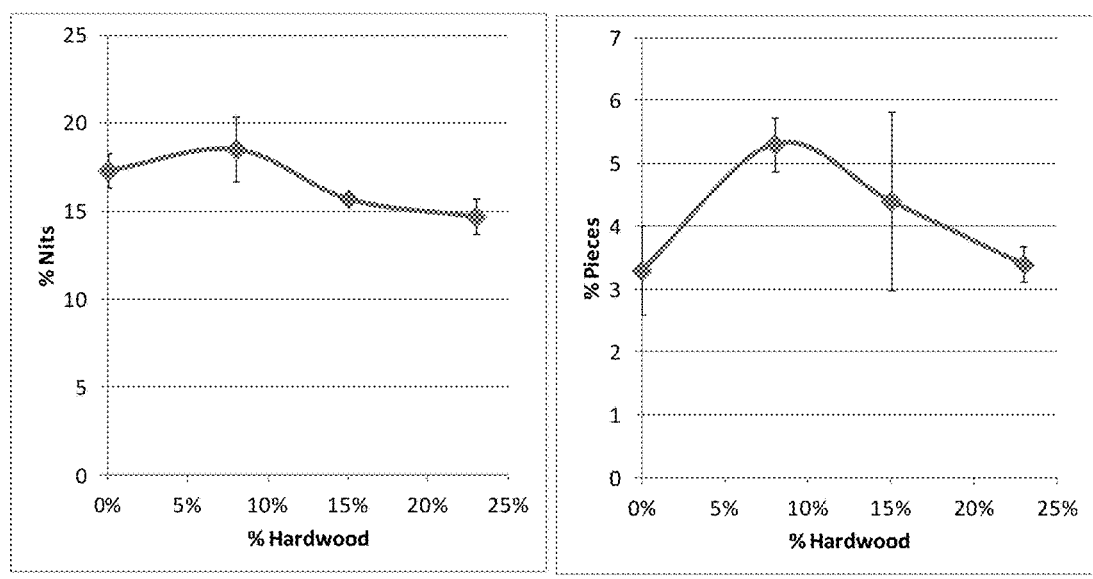
FIG. 5 shows shred quality in percent nits and pieces for exemplary and comparative embodiments.

FIG. 5 shows shred quality in percent nits and pieces for exemplary and comparative embodiments.

Figure 6:
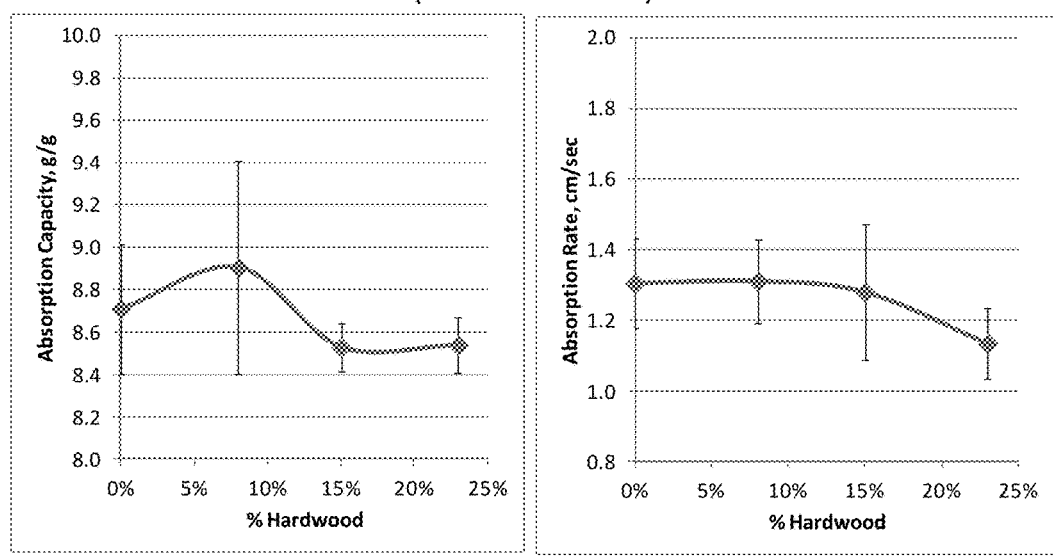
FIG. 6 shows shred absorption in absorption capacity and rate for exemplary and comparative embodiments.

FIG. 6 shows shred absorption in absorption capacity and rate for exemplary and comparative embodiments.

Table 1 shows multi-dose acquisition test data for exemplary and comparative embodiments.

TABLE 1

MULTI-DOSE ACQUISITION TEST—Acquisition Times, seconds

| % HARDWOOD | FIRST DOSE | SECOND DOSE | THIRD DOSE |
| --- | --- | --- | --- |
| 0 | 27.4 | 74.4 | 98.0 |
| 8 | 33.2 | 88.3 | 115.3 |
| 15 | 37.3 | 99.7 | 127.4 |
| 34 | 40.8 | 110.1 | 135.1 |

Table 2 shows multi-dose rewet test data for exemplary and comparative embodiments.

TABLE 2

MULTI-DOSE Rewet Test—Rewet Weight

| % HARDWOOD | SECOND DOSE | THIRD DOSE |
| --- | --- | --- |
| 0 | 5.5 | 7.0 |
| 8 | 5.3 | 6.1 |
| 15 | 5.6 | 6.8 |
| 34 | 5.3 | 6.6 |

The results show that adding as little as 8% hardwood gave a significant improvement in SAP retention The results show that Mullen and Shred Energy are reduced with hardwood substitution The results show that shred quality is maintained, with increased amount of fines in shred The results show that acquisition rate increased with hardwood, but rewet was unaffected.

These results suggest that a small hardwood substitution can provide the benefits of making cores with high SAP content and improved SAP retention, and thinner cores are possible.

From the results shown, it is clear that the examples falling within the scope of the claims inhere superior benefits when compared to those comparative examples.

As used throughout, ranges are used as a short hand for describing each and every value that is within the range, including all subranges therein.

All other references, as well as their cited references, cited herein are hereby incorporated by reference with respect to relative portions related to the subject matter of the present invention and all of its embodiments.

Numerous modifications and variations on the present invention are possible in light of the above teachings. It is, therefore, to be understood that within the scope of the accompanying claims, the invention may be practiced otherwise than as specifically described herein.

What is claimed is:

1. A fluff pulp composition, comprising:
   softwood fibers;
   8 to 23% by weight of hardwood fibers; and
   one or more superabsorbent polymer (SAP),
   wherein the fluff pulp composition has a SAP retention value greater than 75%.

2. The fluff pulp composition of claim 1, wherein the softwood fibers and hardwood fibers are provided in a fluff pulp which comprises a moisture content of ≤15% by weight.

3. The fluff pulp composition of claim 1, wherein the softwood fibers and hardwood fibers are provided in a fluff pulp which comprises a basis weight of 500 to 1100 gsm.

4. The fluff pulp composition of claim 1, in the form of an airlaid core.

5. A core, comprising:
   a fluff pulp, comprising;
   softwood fibers;
   8 to 23% by weight of hardwood fibers; and
   one or more superabsorbent polymer (SAP), wherein the core has a SAP retention value greater than 75%.

6. The core of claim 5, wherein the SAP is selected from the group consisting of starch-acrylonitrile copolymer, hydrolyzed starch-acrylonitrile copolymer, acrylic acid (co)polymer, acrylamide (co)polymer, polyvinyl alcohol, polyacrylate/polyacrylamide copolymers, polyacrylic acid (co)polymers, sodium polyacrylate, ethylene maleic anhydride copolymer, cross-linked carboxymethylcellulose, polyvinyl alcohol copolymer, polyethylene oxide, cross-linked polyethylene oxide, starch grafted copolymer of polyacrylonitrile, salt of one or more thereof, and combination of two or more thereof.

7. The core of claim 5, wherein the SAP is present in an amount ranging from 1 to 85% by weight of the core.

8. The core of claim 5, in the form of an airlaid core.

9. An article comprising the core of claim 5 and a supporting structure or material, wherein the article is selected from the group consisting of an absorbent product, paper product, personal care product, medical product, insulating product, construction product, structural material, cement, food product, veterinary product, packaging product, diaper, tampon, sanitary napkin, gauze, bandage, fire retardant, or a combination thereof.

* * * * *